(12) United States Patent
Bullens et al.

(10) Patent No.: US 8,033,998 B2
(45) Date of Patent: Oct. 11, 2011

(54) DEVICE AND METHOD FOR AUTOMATIC THRESHOLD SETTING

(75) Inventors: Roland W. M. Bullens, Maastricht (NL); Roger Kessels, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 1321 days.

(21) Appl. No.: 11/617,029

(22) Filed: Dec. 28, 2006

(65) Prior Publication Data
US 2008/0161657 A1    Jul. 3, 2008

(51) Int. Cl.
*A61B 5/08* (2006.01)
*A61B 5/05* (2006.01)

(52) U.S. Cl. ......... 600/484; 600/538; 600/529; 600/547

(58) Field of Classification Search .................. 600/300, 600/301, 529, 543, 547, 481, 483, 484, 513
See application file for complete search history.

(56) References Cited

U.S. PATENT DOCUMENTS

| | | | |
|---|---|---|---|
| 5,354,319 A | 10/1994 | Wyborny et al. | |
| 5,987,352 A | 11/1999 | Klein et al. | |
| 6,076,015 A * | 6/2000 | Hartley et al. | 607/20 |
| 6,104,949 A * | 8/2000 | Pitts Crick et al. | 600/547 |
| 6,250,309 B1 | 6/2001 | Krichen et al. | |
| 6,442,433 B1 | 8/2002 | Linberg | |
| 6,480,745 B2 | 11/2002 | Nelson | |
| 6,482,154 B1 | 11/2002 | Haubrich et al. | |
| 6,522,915 B1 | 2/2003 | Ceballos et al. | |
| 6,574,511 B2 | 6/2003 | Lee | |
| 6,599,250 B2 | 7/2003 | Webb et al. | |
| 6,804,656 B1 * | 10/2004 | Rosenfeld et al. | 705/3 |
| 6,949,075 B2 * | 9/2005 | Hatlesad et al. | 600/586 |
| 7,340,296 B2 * | 3/2008 | Stahmann et al. | 600/547 |
| 7,480,528 B2 * | 1/2009 | Brockway et al. | 600/513 |
| 7,578,794 B2 * | 8/2009 | Hatlestad et al. | 600/508 |
| 7,874,992 B2 * | 1/2011 | Cho et al. | 600/483 |
| 7,887,493 B2 * | 2/2011 | Stahmann et al. | 600/529 |
| 7,899,519 B2 * | 3/2011 | Carlson et al. | 600/509 |
| 2006/0025827 A1 * | 2/2006 | Hatlesad et al. | 607/17 |
| 2006/0041280 A1 * | 2/2006 | Stahmann et al. | 607/17 |
| 2006/0258952 A1 * | 11/2006 | Stahmann et al. | 600/547 |
| 2006/0264776 A1 * | 11/2006 | Stahmann et al. | 600/547 |
| 2006/0293609 A1 * | 12/2006 | Stahmann et al. | 600/547 |
| 2007/0055317 A1 * | 3/2007 | Stahmann et al. | 607/23 |
| 2007/0179385 A1 * | 8/2007 | Cho et al. | 600/485 |

\* cited by examiner

*Primary Examiner* — Charles A Marmor, II
*Assistant Examiner* — Navin Natnithithadha
(74) *Attorney, Agent, or Firm* — Stephen W. Bauer; Reed A. Duthler

(57) ABSTRACT

An implantable medical device for detecting physiological events includes a first sensor for sensing a first signal in a patient correlated to a first physiological condition, a second sensor for sensing a second signal in the patient corresponding to a second physiological condition and a third sensor for sensing a third signal in the patient corresponding to a third physiological condition responsive to the second physiological condition. Control circuitry for receiving the first, second and third signals is configured to determine a relationship between the second signal and the third signal, detect a change in the relationship between the second signal and the third signal and determine a threshold in response to detecting the change in the relationship between the second signal and the third signal. A physiological event is detected in response to the first signal crossing the determined threshold.

24 Claims, 5 Drawing Sheets

DEVICE AND METHOD FOR AUTOMATIC THRESHOLD SETTING

TECHNICAL FIELD

The invention relates generally to implantable medical devices and, in particular, to a device and method for automatically setting a threshold for detecting a physiological event.

BACKGROUND

Implantable medical devices are available for monitoring physiological signals of a patient. Physiological signals may be analyzed by the device for automatically detecting an adverse physiological condition or event. The physiological monitoring may be used by the device for controlling automatic delivery of a therapy, such as an electrical stimulation therapy or a drug therapy. The medical device may be provided with a patient alarm for notifying the patient of the presence of the detected physiological event or condition. In response to a patient alarm, the patient takes appropriate action, such as seeking medical attention, as previously advised by a clinician.

Typically a threshold value is defined, which when crossed by a monitored physiological parameter triggers the patient alarm. The threshold for triggering an alarm may be set to a nominal value or a value derived from clinical data relating to a selected patient population. The threshold may not be individualized for a particular patient, potentially resulting in the triggering of false alarms. Such false alarms are inconvenient both to the patient and the treating physician. Accordingly, a method and apparatus are needed for setting an appropriate threshold for individual patients for detecting a physiological condition and triggering a patient alarm.

DETAILED DESCRIPTION

Figure 1:
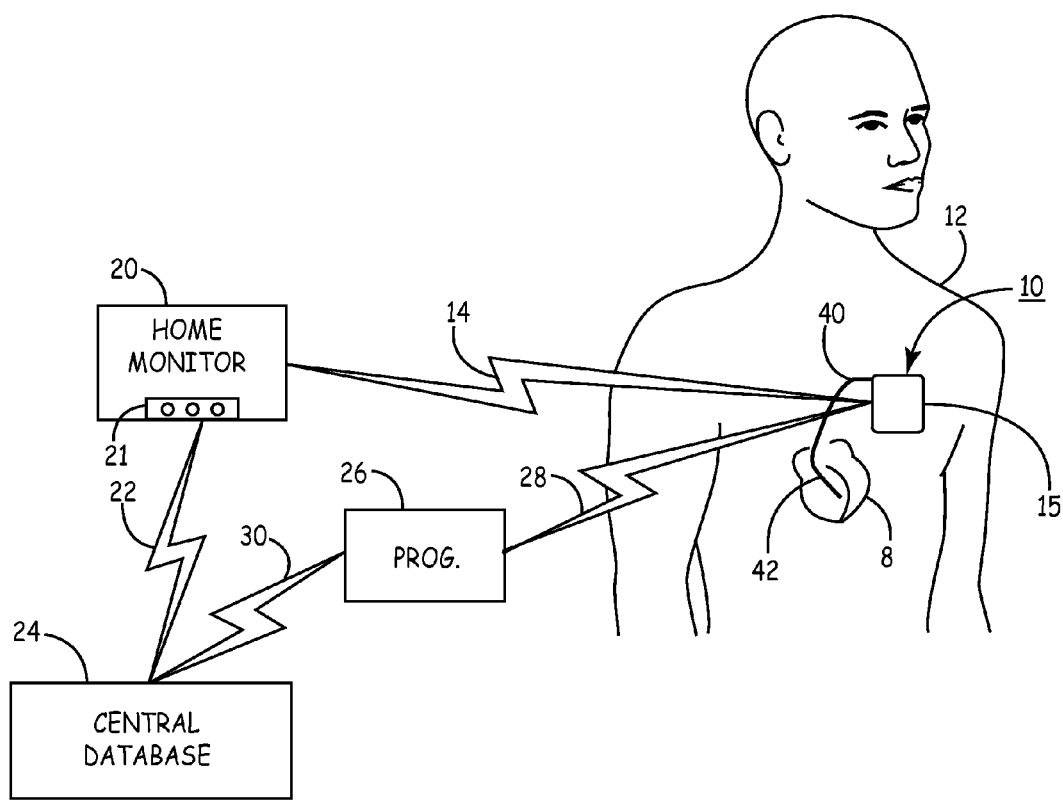
FIG. 1 illustrates an implantable medical device (IMD) system.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 illustrates an implantable medical device (IMD) system. IMD 10 is shown implanted in a patient 12. The simplified illustration of IMD 10 may represent a variety of IMDs such as a cardiac pacemaker, implantable cardioverter defibrillator, hemodynamic monitor, ECG recorder, or a drug delivery device. In alternative embodiments, an IMD may be implemented as an insulin monitor or pump, or a neuromuscular stimulator. IMD 10 may be coupled to one or more fluid delivery catheters or electrical leads 40. In the embodiment shown, lead 40 is used for carrying one or more electrodes and/or other physiological sensors used for monitoring one or more physiological signals and delivering electrical stimulation therapies to the patient's heart 8. IMD 10 may alternatively be embodied as a leadless device wherein sensors and/or electrodes are incorporated in or on the housing of IMD 10. Examples of leadless devices are generally disclosed in U.S. Pat. No. 6,522,915 (Ceballos et al.) and U.S. Pat. No. 5,987,352 (Klein et al.), both of which patents are incorporated herein by reference in their entirety.

Lead 40 is a ventricular lead including a coil electrode 42. Coil electrode 42 may be used in conjunction with IMD housing 15 for delivering cardioversion/defibrillation shocks to a patient. Lead 40 may also be provided with a tip electrode and a ring electrode for sensing cardiac signals and delivering cardiac pacing pulses. In one embodiment of the invention, coil electrode 42 is used in conjunction with IMD housing 15 to measure thoracic impedance for monitoring thoracic fluid level and respiration rate. In patients suffering from congestive heart failure, an increase in pulmonary fluid congestion will result in a decrease in thoracic impedance. Monitoring of thoracic impedance over time allows a trend of worsening or improving thoracic fluid level (pulmonary edema) to be tracked.

In other embodiments lead 40 may be equipped with other physiological sensors such as blood chemistry sensors, temperature sensors, flow sensors, wall motion sensors or the like. Furthermore, while IMD 10 is shown as a cardiac device coupled to the patient's heart 8 via a ventricular lead 40 positioned in the right ventricle, various embodiments of the invention may include other types of implantable medical devices including other sensor configurations for monitoring a physiological signal for detecting a condition or event associated with a change in the monitored signal.

IMD 10 is provided with an antenna and associated circuitry, as will be described below, for establishing a communication link 14 with home monitor 20 and a communication link 28 with a physician programmer 26. Home monitor 20 may include a user interface 21 that allows patient 12 or a caregiver to transmit commands or signals to IMD 10 using home monitor 20. Home monitor 20 may be enabled to generate a patient alarm in response to receiving a signal from IMD 10 corresponding to a detected physiological condition or event. A patient alarm may be provided as a visual display and/or audible sounds.

Home monitor 20 may be configured to receive data from IMD 10 for transmission to a central database 24 to enable remote monitoring or remote follow up of patient 12. In some embodiments, home monitor 20 may be enabled to transmit data received from central database 24 corresponding to operating code or control parameters used by IMD 10.

IMD 10 is further enabled for bidirectional communication with a physician programmer 26 via telemetry link 28. Physician programmer 26 is generally located in a health care facility, such as a clinic or hospital, for use by medical personnel and is typically enabled for full IMD programming and interrogation functions. Either of home monitor 20 and programmer 26 may be used to send a signal to IMD 10 confirming or indicating a particular patient condition. As will be further described below, home monitor 20 or programmer 26 may be used to confirm a resting state and an active state of the patient for use by IMD 10 in setting a threshold for detecting a physiological event.

Home monitor 20 and/or programmer 26 may optionally be adapted to communicate with a central database 24 to allow transfer of data received from IMD 10 to the central database 24. A central database may be an Internet-based or other networked database used for remote patient monitoring. Home monitor 20 may transfer data via a communication link 22, which may be established via the Internet, a local area network, a wide area network, a telecommunications network or other appropriate communications network and may be a wireless communication link. Likewise, programmer 26 may receive data from IMD 10 and transfer the data to central database 24 using a communication link 30. Examples of remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety. Data relating to the detection of a physiological event or the generation of a patient alarm may be transferred to the central database 24 from IMD 10.

Figure 2:
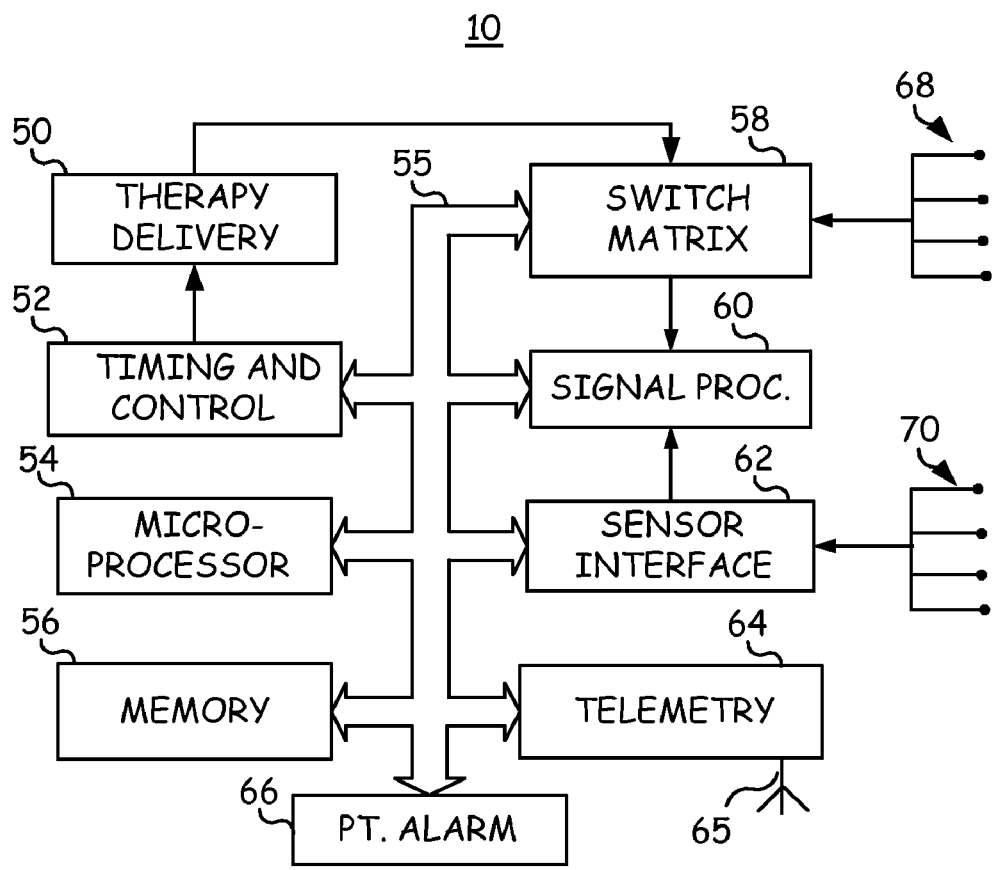
FIG. 2 is a block diagram of the IMD shown in FIG. 1.

FIG. 2 is a functional block diagram of IMD 10 shown in FIG. 1. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 may also be used for sensing electrical signals within the body, such as cardiac signals, or for measuring impedance, such as thoracic impedance for fluid monitoring as described above. Cardiac electrical signals are sensed using any of electrodes 68 for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias. Electrodes 68 may be used for measuring impedance signals for monitoring pulmonary congestion, respiration or heart chamber volume. Any of these signals may be used to detect a change indicating a worsening pathologic condition, which may be used in controlling IMD functions and triggering a patient alarm. Impedance signals can also be used for monitoring lead performance and detecting lead-related problems.

IMD 10 further includes physiological sensors 70. Physiological sensors 70 may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological events or changes in monitored physiological conditions may be defined as triggering conditions for a patient alarm to be generated by IMD 10.

In one embodiment of the invention, electrodes 68 are used for sensing thoracic impedance for monitoring thoracic fluid level and for determining a respiration rate. Sensors 70 include an activity sensor for monitoring the physical activity of the patient. As will be described in detail below, the respiration rate response to an increase in activity level is used in setting a thoracic impedance measurement threshold for detecting a worsening pulmonary edema condition. In congestive heart failure patients, worsening pulmonary congestion or edema is typically accompanied by shortness of breath. Patients often experience shortness of breath during activity several days prior to hospitalization due to heart failure symptoms. Timing and control 52 controls the timing of respiration rate measurements made for determining a respiration rate response to activity for use in setting a thoracic fluid level threshold corresponding to a detected shortness of breath.

As used herein, "respiration rate response" generally refers to the rate of respiration occurring in response to a change in patient activity. An "increased respiration rate response" refers to a pathologically high respiration rate in response to a change in patient activity, also referred to herein as "shortness of breath". The terms "pulmonary edema", "pulmonary congestion", and "lung congestion" generally refer to conditions associated with an increase in thoracic fluid level, typically associated with congestive heart failure.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 is used to store operating commands and data for controlling device operation and for later retrieval to diagnose device function or patient condition. In accordance with the various embodiments of the present invention, parameter values or thresholds defining one or more patient alarm conditions may be stored in memory 56 and used by microprocessor 54 in triggering a patient alarm.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. IMD telemetry circuitry 64 may be used for receiving an externally generated signal, for example from programmer 26 or home monitor 20 (shown in FIG. 1) for confirming an activity level of a patient for use by IMD 10 in determining a baseline relationship between a patient's respiration rate and activity level.

In some embodiments, telemetry circuitry may require patient intervention to initiate or enable transfer/receipt of data to/from an external device. For example, telemetry circuitry 64 may require the use of an external programming head containing an external antenna to be positioned over IMD 10 as generally disclosed in U.S. Pat. No. 5,354,319 issued to Wyborny et al. Telemetry circuitry 64 may require manual "waking up" by the patient to enable data transmission or may require the patient to be within a limited communication range from the external device. In other embodiments, long range telemetry systems may be used allowing data to be transferred between IMD 10 and an external device automatically without intervention by the patient or another operator. Long-range telemetry systems are generally disclosed in U.S. Pat. No. 6,482,154 issued to Haubrich et al., incorporated herein by reference in its entirety.

IMD 10 includes patient alarm circuitry 66 for generating audible tones, a perceptible vibration, muscle stimulation or other sensory stimulation for notifying the patient that an alarm condition has been detected by IMD 10. Alternatively, a patient alarm may be provided by home monitor 20 (FIG. 1) in response to a signal received from IMD 10 as described previously.

Figure 3:
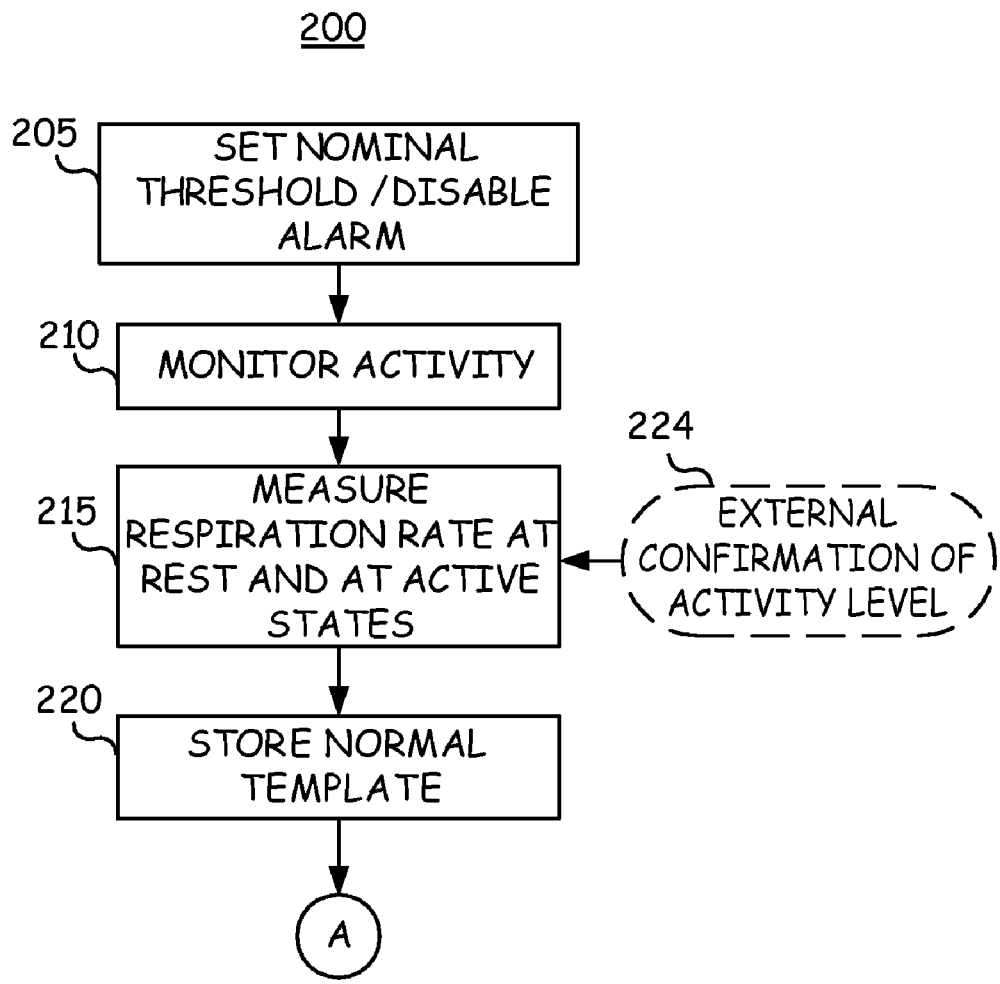
FIG. 3 is a flow chart of a method for storing a normal template relationship between monitored physiological parameters according to one embodiment of the invention.

FIG. 3 is a flow chart 200 of a method for storing a normal template relationship between monitored physiological parameters according to one embodiment of the invention. Detection of a deviation or divergence from this normal relationship will be used for setting at threshold for detecting a pathological event. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 205, a patient alarm may be disabled to prevent delivery of false alarms until an appropriate threshold has been determined for the individual patient. Alternatively, a nominal threshold may be set for triggering a patient alarm in response to detecting a physiological event. A physician may initially select a very high threshold (or low threshold depending on the particular application) to prevent false alarms but still provide an alarm in response to a significantly worsening condition.

At block 210, an activity signal is monitored. In one embodiment, method 200 is performed to determine a normal relationship between activity and respiration rate for an individual patient. Shortness of breath is often the first symptom a patient experiences when lung congestion is worsening due to heart failure. As such, automatic detection of an increased respiration rate response to activity can be used in determining a thoracic fluid threshold level for triggering a patient alarm to warn the patient of worsening pulmonary edema.

At block 215, a respiration rate is measured during at least 2 different activity levels. Typically a resting respiration rate and a respiration rate at an increased activity level is measured. The resting respiration rate may be measured at night while the patient is expected to be sleeping or any time the activity sensor signal indicates a baseline or resting activity level. A resting activity level may correspond to lying down or sitting. The respiration rate may be measured on a single respiration cycle or multiple cycles for determining a mean or average respiration rate. Respiration rate may be measured or derived from any signal known to fluctuate in response to respiratory movement or pressure changes, including impedance signals, pressure signals and motion signals, e.g. motion signals obtained from an accelerometer signal. In one embodiment, a thoracic impedance signal that is also used to monitor thoracic fluid level is used for determining a respiration rate. The respiration rate may be determined by measuring the time intervals between consecutive signal peaks associated with the respiration cycle. Any known method for determining a respiration rate by an implantable medical device may be implemented and is considered within the scope of the present invention.

The resting respiration rate may be measured after a resting state has been detected for a minimum interval of time in order to ensure that the patient's respiration rate has reached a resting level. For example, the patient may be engaged in physical activity and then lay down to rest. The activity signal will immediately indicate a resting state however the respiration rate response will lag behind the change in activity. Likewise, the patient may change from a resting state to an active state. The activity signal will immediately respond to the increase in activity, however the rise in respiration rate in response to sustained activity will lag somewhat behind the onset of activity. As such, control circuitry may initiate a respiration rate measurement at a predetermined time interval after a sustained level of activity (rest or active) is detected.

In alternative embodiments, the respiration rate may be immediately monitored upon initiation of a particular activity level (rest or active). The control circuitry may then determine when the respiration rate has reached a steady state level or a maximum time has been reached during a sustained level of the activity. In still other embodiments, the respiration rate is monitored throughout or for a predetermined interval of time during a sustained level of activity. A maximum, minimum, average, or mean respiration rate during the sustained activity level may then be determined.

The activity level may optionally be confirmed using an external programming device as indicated by block 224. In some embodiments, the template relationship is determined and stored according to method 200 while the patient is under medical supervision, for example in a clinic or hospital. As such, a clinician may provide an external signal indicating at least two activity level states at which a respiration rate should be measured. The respiration rate may be measured immediately in response to receiving the external signal or the respiration rate may be measured after the implanted device has confirmed that the activity level has remained at the same level for a predetermined period of time after receiving the external signal and/or the respiration rate has reached a steady state.

After measuring the respiration rate for at least two activity levels, the normal template is stored at block 220 representing a normal respiration rate response for a given patient. A deviation from this normal response may correspond to abnormal breathing associated with heart failure.

Figure 4:
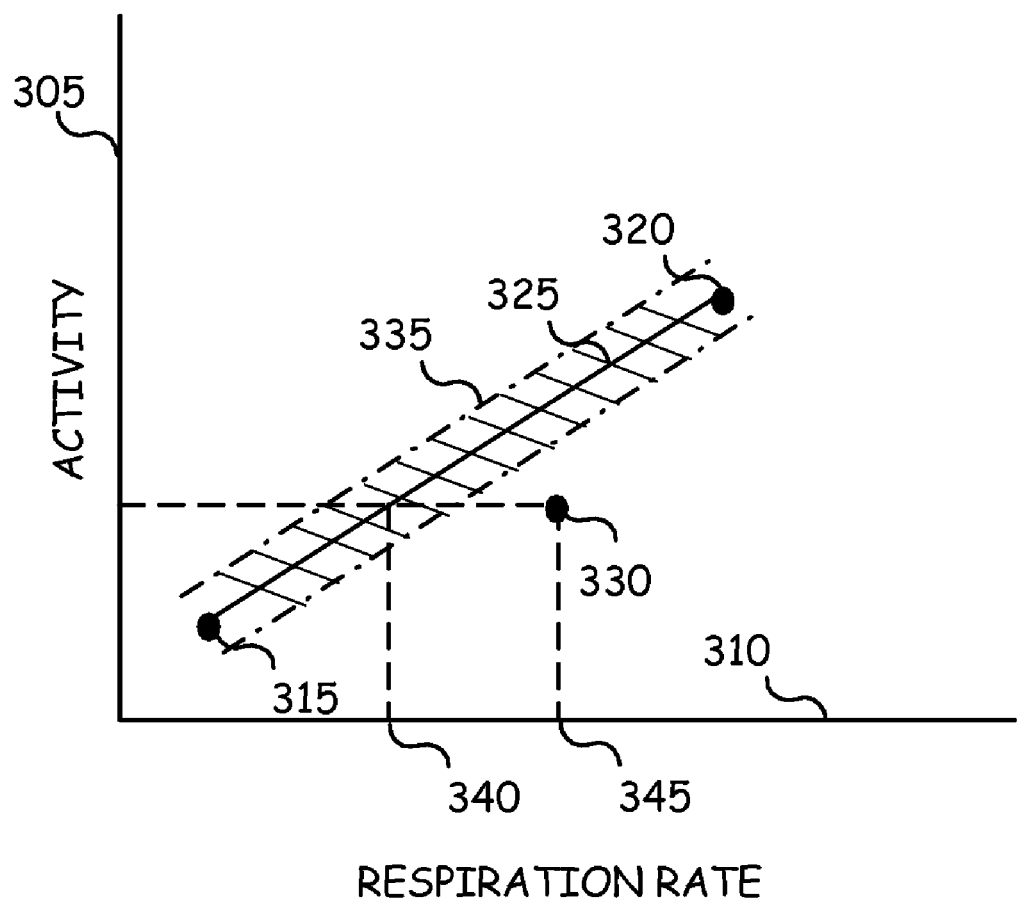
FIG. 4 is a plot of activity versus respiration rate.

FIG. 4 is a hypothetical plot of a relationship between activity 305 and respiration rate 310. A normal respiration rate response template 325 is determined by measuring the respiration rate at a first activity level 315 and at a second activity level 320. It is recognized that additional points may be determined for determining template 325 by measuring the respiration rate at additional activity levels. Typically, the first activity level 315 will be a resting level and the second activity level will be an active state. However, the first activity level 315 may correspond to a low level of activity such as standing or walking and the second activity level 320 may correspond to a higher activity level such as fast walking, jogging or cycling. It is not necessary for the patient achieve a specific level of activity in order to measure the respiration rate for obtaining normal template 325, just that at least two different activity levels are achieved. It may be desirable to measure the respiration rate at two activity levels that are substantially different so that the normal template 325 may be interpolated over a range of activity levels. The normal template 325 may also be extrapolated for predicting a respiration rate at activity levels lower than the first activity level 315 and higher than the second activity level 320.

As will be further described below, detection of a deviation from the normal respiration rate response template 325 is used in setting a thoracic fluid level alarm. After storing the normal template 325, a respiration rate 345 corresponding to activity level 330 is measured to be higher than the expected respiration rate 340 predicted by the normal template 325. This increase in the respiration rate response to activity may reflect shortness of breath due to increased thoracic congestion. An increase in the respiration response to exercise, i.e. shortness of breath, may be detected when the respiration rate 345 is a predetermined percentage greater than a predicted respiration rate 340 or when the respiration rate and activity plotted point 330 falls outside a predetermined range 335 of the normal template curve 325. Range 335 may be defined as a standard deviation of the template curve 325. Other methods may be used for defining when a measured respiration rate 345 is considered significantly different than a normal template response, indicating shortness of breath.

Determination of a normal template relationship between activity and respiration rate may be repeated in order to update the stored template as appropriate. A patient's physical fitness will influence the respiration rate response to activity. As such, if a patient's heart failure condition improves, allowing the patient to be more active, the patient's physical condition may improve, shifting the normal template curve 325 to the left. Likewise, the physical fitness of the patient may worsen, shifting the normal template curve 325 to the right or altering the general slope or shape of the curve. Method 200 may be repeated on a periodic basis or upon a programmed schedule in order to update the normal template 325.

Figure 5:
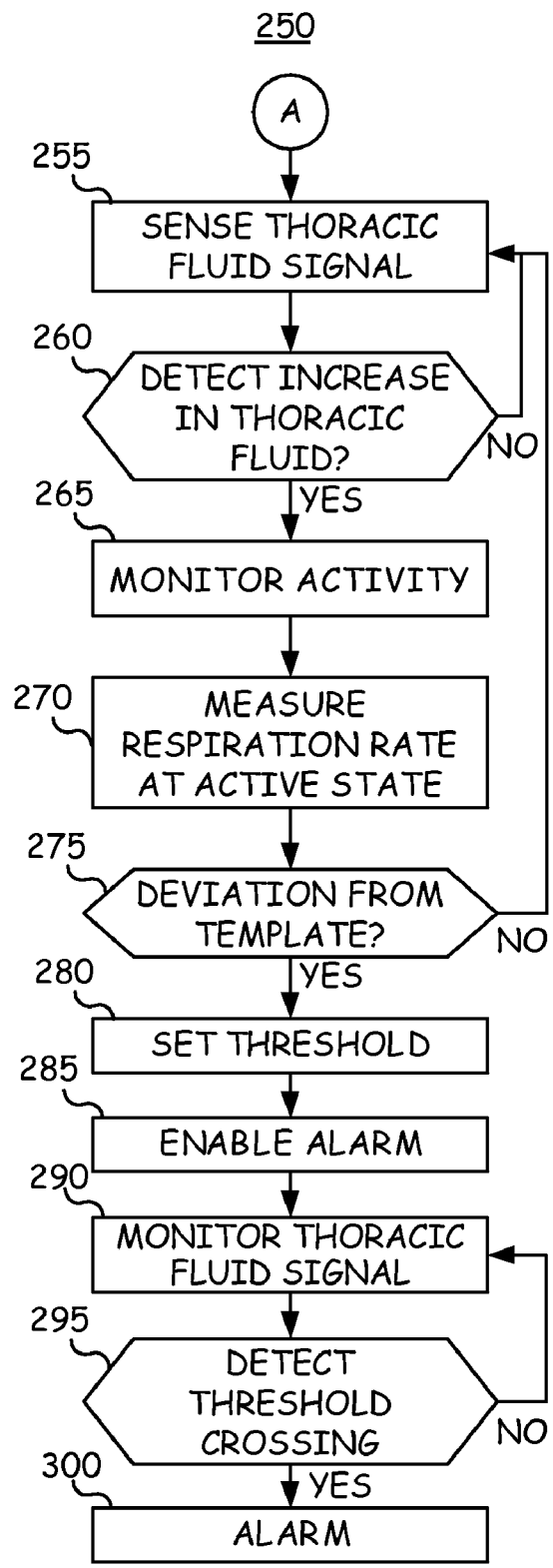
FIG. 5 is a flow chart of a method for automatically setting an event detection threshold according to one embodiment of the invention.

FIG. 5 is a flow chart 250 of a method for automatically setting an event detection threshold according to one embodiment of the invention. After storing a normal activity/respiration rate response template at block 220 of method 200, a signal correlated to thoracic fluid level is sensed at block 255 of method 250. As described previously, a thoracic impedance signal may be sensed for monitoring thoracic fluid level. In alternative embodiments, any signal responsive to thoracic fluid level changes may be monitored. The sensed signal may be analyzed to determine a parameter correlated to thoracic fluid level.

An increase in thoracic fluid level detected at block 260 triggers activity monitoring at block 265. Initially any increase in the thoracic fluid level triggers activity and respiration monitoring. Any change measurable by the resolution of the monitored signal or parameter indicating an increase in thoracic fluid may trigger measurement of the respiration response to activity. Alternatively, some minimum change may be required to trigger respiration rate measurements. Methods or algorithms used for detecting an increase in fluid level will depend on the sensor used. In one embodiment, a daily mean impedance is determined from a thoracic impedance signal. An increase in the daily mean impedance will trigger activity monitoring at block 265. In some embodiments, activity may be continuously monitored, for example for controlling a pacing rate.

At block 270, respiration rate is measured at the current level of activity upon detection of an increase in thoracic fluid level. The respiration rate and corresponding activity level are compared to the stored normal template at decision block 275. Alternatively, the respiration rate measurement at block 270 is triggered after a predetermined minimum level of activity is sensed at block 265, for example an activity level corresponding to standing or walking. Typically the respiration rate will be measured during an active state rather than a resting state since the onset of shortness of breath symptoms will generally first become noticeable upon exertion. However, monitoring respiration rate at a resting state for detecting a change in respiration rate response is within the scope of the invention. An increased respiration rate at rest can also be recognized as a deviation from the normal respiration template at decision block 275 and used in setting a threshold at block 280.

If the respiration rate measured at an associated activity level matches the stored normal template at block 275, method 250 continues to monitor the thoracic fluid signal at block 255. An additional increase in thoracic fluid level will trigger activity/respiration rate measurements. In alternative embodiments, once an increase in thoracic fluid level has triggered respiration rate monitoring, the respiration rate response will continue to be monitored until a threshold is set. For example, the respiration rate may be measured each time the activity reaches a predetermined level. Alternatively, the respiration rate may be measured daily, or on another periodic basis, during an active state.

If the measured respiration rate is determined to deviate from the stored template, indicating shortness of breath, a patient alarm threshold is set at block 280 corresponding to the detected increased thoracic fluid level. For example, if a daily mean impedance is found to decrease, at decision block 260 and a respiration rate measured at block 270 is determined to deviate from the previously stored normal respiration rate response template, the decreased daily mean impedance measurement is stored as a patient alarm threshold at block 280. A patient alarm may be immediately generated at block 285. If the patient alarm had initially been disabled until a patient-specific threshold has been set, the patient alarm is enabled at block 285.

In other embodiments, a threshold may be calculated as a percentage of the increased thoracic fluid level. A threshold may alternatively be set as a thoracic fluid level measured at a predetermined time interval before or after the increased thoracic fluid level was detected. The threshold may also be set as an average of thoracic fluid level measurements determined over a predetermined time interval including the increase in the thoracic fluid level. For example, three daily mean impedance measurements may be averaged to determine a threshold. It is recognized that numerous algorithms or methods may be used for determining a threshold as a function of an increased thoracic fluid is recognized that numerous algorithms or methods may be used for determining a threshold as a function of the increased thoracic fluid level detected in combination with shortness of breath.

After setting the threshold and enabling the alarm, thoracic fluid level monitoring continues at block 290. If the thoracic fluid level crosses the threshold, as determined at decision block 295, the patient alarm is generated at block 300. The patient responds to the alarm in accordance with physician instructions, which may include seeking medical attention and/or adjusting a medication.

It is recognized that various embodiments may include multiple sensor signals, multiple parameters, and/or other methods for computing a threshold based on a thoracic fluid level signal or parameter measured at the time of a detected shortness of breath. Furthermore, it is recognized that in other embodiments, a threshold determined in response to automatically detecting shortness of breath may be used for triggering other device functions. For example, in some embodiments, the threshold may be used to trigger delivery or adjustment of a therapy. The methods for computing the threshold will take into account the desired warning time that a patient/clinician will have prior to manifestation of a serious clinical event, such as hospitalization due to heart failure symptoms. By triggering the patient alarm and/or other device functions in advance of the serious event, the event may be prevented or at least lessened in severity.

Thus, an implantable medical device system and associated methods have been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
a first sensor for sensing a first signal in a patient correlated to a first physiological condition;
a second sensor for sensing a second signal in the patient corresponding to a second physiological condition;
a third sensor for sensing a third signal in the patient corresponding to a third physiological condition responsive to the second physiological condition; and
control circuitry for receiving the first, second and third signals and being configured to determine a relationship between the second signal and the third signal, detect a change in the relationship between the second signal and the third signal, determine a threshold in response to detecting the change in the relationship between the second signal and the third signal, and detect an event in response to the first signal crossing the determined threshold;
wherein the first sensor signal is correlated to a thoracic fluid level, the second sensor signal is correlated to patient activity, and the third sensor signal is correlated to respiration rate, and
wherein detecting a change in the relationship between the second and third signals includes determining an activity level in response to sensing an increase in thoracic fluid level and sensing an increase in a respiration rate response to activity level compared to a previously measured respiration rate response, and
wherein determining the threshold includes determining a first sensor signal level corresponding to the increase in the respiration rate response.

2. An implantable medical device according to claim 1 further comprising alarm circuitry for generating an alarm in response to detection of the event.

3. An implantable medical device according to claim 1 wherein the first sensor signal is an impedance signal.

4. An implantable medical device according to claim 1 wherein determining the relationship between the second signal and the third signal includes measuring the third signal in response to the second signal corresponding to a first activity level and measuring the third signal in response to the second signal corresponding to a second activity level.

5. An implantable medical device according to claim 1 wherein detecting a change in the relationship between the second signal and the third signal includes sensing the second signal and the third signal in response to a change in the first signal.

6. An implantable medical device according to claim 5 wherein the change in the first signal corresponds to an increase in thoracic fluid level.

7. A method comprising employing an implantable medical device to perform the following steps:
sensing a first signal in a patient correlated to a first physiological condition;
sensing a second signal in the patient corresponding to a second physiological condition;
sensing a third signal in the patient corresponding to a third physiological condition responsive to the second physiological condition;
determining a relationship between the second signal and the third signal,
detecting a change in the relationship between the second signal and the third signal,
determining a threshold in response to the detected change in the relationship between the second signal and the third signal, and
detecting an event in response to the first signal crossing the determined threshold;
wherein the first signal is correlated to a thoracic fluid level, the second signal is correlated to patient activity, and the third signal is correlated to respiration rate, and
wherein detecting a change in the relationship between the second and third signals includes determining an activity level in response to sensing an increase in thoracic fluid level and sensing an increase in a respiration rate response to the activity level compared to a previously measured respiration rate response, and
wherein determining the threshold includes determining a first sensor signal level corresponding to the increase in the respiration rate response.

8. A method according to claim 7, further comprising generating an alarm in response to detection of the event.

9. A method according to claim 7, wherein the first signal is an impedance signal.

10. A method according to claim 7, wherein determining the relationship between the second signal and the third signal includes measuring the third signal in response to the second signal corresponding to a first activity level and measuring the third signal in response to the second signal corresponding to a second activity level.

11. A method according to claim 7, wherein detecting a change in the relationship between the second signal and the third signal includes sensing the second signal and the third signal in response to a change in the first signal.

12. A method according to claim 11, wherein the change in the first signal corresponds to an increase in thoracic fluid level.

13. A non-transitory computer-readable medium for storing a set of instructions which when implemented in an implantable medical device system including a microprocessor cause the system to:
sense a first signal in a patient correlated to a first physiological condition;
sense a second signal in the patient corresponding to a second physiological condition;
sense a third signal in the patient corresponding to a third physiological condition responsive to the second physiological condition;

determine a relationship between the second signal and the third signal, detect a change in the relationship between the second signal and the third signal, determine a threshold in response to the detected change in the relationship between the second signal and the third signal, and detect an event in response to the first signal crossing the determined threshold;

wherein the first signal is correlated to a thoracic fluid level, the second signal is correlated to patient activity, and the third signal is correlated to respiration rate, and wherein instructions for detecting a change in the relationship between the second and third signals include instructions for determining an activity level in response to sensing an increase in thoracic fluid level and sensing an increase in a respiration rate response to the activity level compared to a previously measured respiration rate response, and wherein instructions for the threshold include instructions for determining a first sensor signal level corresponding to the increase in the respiration rate response.

14. A computer-readable medium according to claim 13, further comprising instructions which cause the system to generate an alarm in response to detection of the event.

15. A computer-readable medium according to claim 13, wherein the first signal is an impedance signal.

16. A computer-readable medium according to claim 13, wherein instructions for determining the relationship between the second signal and the third signal include instructions for measuring the third signal in response to the second signal corresponding to a first activity level and measuring the third signal in response to the second signal corresponding to a second activity level.

17. A computer-readable medium according to claim 13, wherein instructions for detecting a change in the relationship between the second signal and the third signal include instructions for sensing the second signal and the third signal in response to a change in the first signal.

18. A computer-readable medium according to claim 17, wherein the change in the first signal corresponds to an increase in thoracic fluid level.

19. An implantable medical device, comprising:
means for sensing a first signal in a patient correlated to a first physiological condition;
means for sensing a second signal in the patient corresponding to a second physiological condition;
means for sensing a third signal in the patient corresponding to a third physiological condition responsive to the second physiological condition;
means for determining a relationship between the second signal and the third signal,
means for detecting a change in the relationship between the second signal and the third signal,
means for determining a threshold in response to the detected change in the relationship between the second signal and the third signal, and
means for detecting an event in response to the first signal crossing the determined threshold;
wherein the first sensor signal is correlated to a thoracic fluid level, the second sensor signal is correlated to patient activity, and the third sensor signal is correlated to respiration rate, and
wherein detecting a change in the relationship between the second and third signals includes determining an activity level in response to sensing an increase in thoracic fluid level and sensing an increase in a respiration rate response to activity level compared to a previously measured respiration rate response, and
wherein determining the threshold includes determining a first sensor signal level corresponding to the increase in the respiration rate response.

20. An implantable medical device according to claim 19, further comprising alarm circuitry for generating an alarm in response to detection of the event.

21. An implantable medical device according to claim 19, wherein the first sensor signal is an impedance signal.

22. An implantable medical device according to claim 19, wherein determining the relationship between the second signal and the third signal includes measuring the third signal in response to the second signal corresponding to a first activity level and measuring the third signal in response to the second signal corresponding to a second activity level.

23. An implantable medical device according to claim 19, wherein detecting a change in the relationship between the second signal and the third signal includes sensing the second signal and the third signal in response to a change in the first signal.

24. An implantable medical device according to claim 23, wherein the change in the first signal corresponds to an increase in thoracic fluid level.

* * * * *